United States Patent
Ginn

(10) Patent No.: US 9,492,150 B2
(45) Date of Patent: *Nov. 15, 2016

(54) APPARATUS AND METHODS FOR SEALING VASCULAR PUNCTURES

(75) Inventor: Richard S. Ginn, San Jose, CA (US)

(73) Assignee: Cardinal Health Switzerland 515 GmbH (CH)

(*) Notice: Subject to any disclaimer, the term of this patent is extended or adjusted under 35 U.S.C. 154(b) by 0 days.

This patent is subject to a terminal disclaimer.

(21) Appl. No.: 13/316,090

(22) Filed: Dec. 9, 2011

(65) Prior Publication Data

US 2012/0083830 A1    Apr. 5, 2012

Related U.S. Application Data

(60) Continuation of application No. 12/200,459, filed on Aug. 8, 2005, now Pat. No. 8,075,587, which is a division of application No. 10/423,133, filed on Apr. 24, 2003, now Pat. No. 7,083,635, which is a continuation of application No. 09/931,676, filed on Aug. 15, 2001, now Pat. No. 6,623,509, which is a continuation-in-part of application No. 09/866,548, filed on May 25, 2001, now Pat. No. 6,663,655, which is a continuation-in-part of application No. 09/738,431, filed on Dec. 14, 2000, now Pat. No. 6,846,319.

(51) Int. Cl.
*A61B 17/08* (2006.01)
*A61B 17/00* (2006.01)
*A61B 10/00* (2006.01)

(52) U.S. Cl.
CPC .... *A61B 17/0057* (2013.01); *A61B 2010/0003* (2013.01); *A61B 2017/00004* (2013.01); *A61B 2017/00637* (2013.01); *A61B 2017/00654* (2013.01); *A61B 2017/00898* (2013.01)

(58) Field of Classification Search
CPC ............... A61B 2017/00898; A61B 17/0057; A61B 2017/00004; A61B 2017/00637; A61B 2017/00654
USPC ........ 606/231, 232; 604/6.1, 5.01, 9, 41, 43, 604/256, 29
See application file for complete search history.

(56) References Cited

U.S. PATENT DOCUMENTS 4,085,757 A * 4/1978 Pevsner ................... 606/195
4,525,157 A * 6/1985 Vaillancourt ............. 604/510

(Continued)

OTHER PUBLICATIONS

Office Action in corresponding Canadian Patent Application No. 2,733,845 dated Dec. 16, 2013.

*Primary Examiner* — Gregory Anderson
*Assistant Examiner* — Christina Lauer

(57) ABSTRACT

An apparatus for sealing a passage through tissue communicating with a blood vessel includes a bioabsorbable plug member coupled to the distal end of a carrier member. The plug member includes a lumen extending therethrough that communicates with a lumen extending through the carrier member. A sealing member is disposed in the plug member lumen for sealing the lumen. A guide member is slidable into the lumen such that edges of a groove extending between proximal and distal portions of the guide member engage a wall of the lumen to define a bleed back lumen. The guide member is inserted into the passage until the distal portion enters the vessel. The plug member is advanced over the guide member until the plug member enters the vessel, whereupon blood enters the bleed back lumen to identify the location of the vessel relative to the plug member.

18 Claims, 8 Drawing Sheets

(56) References Cited

U.S. PATENT DOCUMENTS

| | | | |
|---|---|---|---|
| 5,275,616 A * | 1/1994 | Fowler | 606/213 |
| 5,292,332 A * | 3/1994 | Lee | A61B 17/0057 |
| | | | 606/213 |
| 5,320,639 A * | 6/1994 | Rudnick | 606/213 |
| 5,342,393 A * | 8/1994 | Stack | 606/213 |
| 5,871,474 A * | 2/1999 | Hermann et al. | 604/256 |
| 5,976,174 A * | 11/1999 | Ruiz | 606/213 |
| 6,663,655 B2 * | 12/2003 | Ginn et al. | 606/213 |
| 2002/0026208 A1 | 2/2002 | Roe et al. | |

* cited by examiner

APPARATUS AND METHODS FOR SEALING VASCULAR PUNCTURES

This application is a continuation of application Ser. No. 11/200,459 filed on Aug. 8, 2005, which is a divisional of application Ser. No. 10/423,133 filed on Apr. 24, 2003, which is a continuation of application Ser. No. 09/931,676, filed Aug. 15, 2001, which is a continuation-in-part of application Ser. No. 09/866,548, filed May 25, 2001, which is a continuation-in-part of application Ser. No. 09/738,431, filed Dec. 14, 2000, the disclosures of which are expressly incorporated herein by reference.

FIELD OF THE INVENTION

The present invention relates generally to apparatus and methods for sealing or closing passages through tissue, and more particularly to devices for sealing punctures or other openings communicating with body lumens, such as blood vessels, and to apparatus and methods for delivering such devices.

BACKGROUND

Catheterization and interventional procedures, such as angioplasty or stenting, generally are performed by inserting a hollow needle through a patient's skin and muscle tissue into the vascular system. A guide wire may then be passed through the needle lumen into the patient's blood vessel accessed by the needle. The needle may be removed, and an introducer sheath may be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introduction of various devices into the vessel, while minimizing trauma to the vessel wall and/or minimizing blood loss during a procedure.

Upon completion of the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,122,974, issued to Kensey et al., describe the use of a biodegradable plug that may be delivered through an introducer sheath into a puncture site. When deployed, the plug may seal the vessel and provide hemostasis. Such devices, however, may be difficult to position properly with respect to the vessel, which may be particularly significant since it is generally undesirable to expose the plug material, e.g., collagen, within the bloodstream, where it may float downstream and risk causing an embolism.

Another technique has been suggested that involves percutaneously suturing the puncture site, such as that disclosed in U.S. Pat. No. 5,304,184, issued to Hathaway et al. Percutaneous suturing devices, however, may require significant skill by the user, and may be mechanically complex and expensive to manufacture.

Staples and surgical clips have also been suggested for closing wounds or other openings in tissue. For example, U.S. Pat. Nos. 5,007,921 and 5,026,390, issued to Brown, disclose staples that may be used to close a wound or incision. In one embodiment, an "S" shaped staple is disclosed that includes barbs that may be engaged into tissue on either side of the wound. In another embodiment, a ring-shaped staple is disclosed that includes barbs that project from the ring. These staples, however, have a large cross-sectional profile and therefore may not be easy to deliver through a percutaneous site to close an opening in a vessel wall.

In addition, skin seals have been proposed that may be threaded into an opening in skin. For example, U.S. Pat. No. 5,645,565, issued to Rudd et al., discloses a surgical plug that may be screwed into a puncture to seal the puncture. The surgical plug includes an enlarged cap and a threaded shaft that extends from the cap. During an endoscopic procedure, the plug may be threaded into an opening through skin until the cap engages the surface of the skin. The plug is intended to seal the opening communicating with a body cavity to prevent insufflation fluid from leaking from the cavity. Such plugs, however, may only be used at the surface of the skin, and may not be introduced through tissue, for example, to seal an opening in the wall of a blood vessel or other subcutaneous region.

Accordingly, devices for sealing punctures or other passages through tissue, e.g., an opening into a blood vessel, would be considered useful.

SUMMARY OF THE INVENTION

The present invention is directed to apparatus and methods for sealing or closing passages through tissue, such as punctures communicating with blood vessels or other body lumens.

In accordance with one aspect of the present invention, an apparatus is provided for sealing a passage through tissue that includes an elongate guide member, a carrier member, and a plug member. The guide member includes a groove in an outer wall of the guide member that extends between proximal and distal portions of the guide member. The carrier member includes proximal and distal ends, and a first lumen extending between the proximal and distal ends.

A plug member, e.g., formed from bioabsorbable material, may be carried on the distal end of the carrier member. The plug member may be releasable from the distal end of the carrier member, e.g., by cooperating connectors, and/or an actuator, or may be substantially permanently attached to the carrier member. The plug member includes a second lumen extending therethrough that communicates with the first lumen, and may include a sealing member disposed in the second lumen for substantially sealing the second lumen from fluid flow therethrough. The plug member may include a substantially smooth outer surface, or may include a helical thread on its outer surface. Preferably, the plug member has a cross-section larger than a cross-section of the carrier member, e.g., to minimize dilation of a passage through which the carrier member is inserted.

The guide member is slidable into the first and second lumens such that edges of the groove substantially engage walls of the first and second lumens to define a bleed back lumen.

In accordance with another aspect of the present invention, a method is provided for sealing a passage through tissue communicating with a body lumen, e.g., a puncture communicating with a blood vessel. The passage may be used to access the body lumen, e.g., to perform an endovascular procedure within the patient's body. Upon completion of the procedure, any instruments received through the passage may be removed, although an introducer sheath and/or guidewire may remain in place through the passage into the vessel.

An elongate member including a groove extending between its proximal and distal portions may be inserted into the passage, e.g., through the introducer sheath or over the guidewire, until the distal portion enters the body lumen. The introducer sheath may be removed (if used), and a plug member disposed on a carrier member may be advanced over the elongate member with the elongate member received in a lumen of the plug member such that the groove and the lumen together define a bleed back lumen. The plug member may include an external thread, and consequently the carrier member may be rotated to thread the plug member into the passage.

When the plug member enters the body lumen, fluid from the body lumen may enter the bleed back lumen to identify the location of the body lumen with respect to the plug member. In one embodiment, a first fluid flow rate through the groove may be detected when the distal portion of the elongate member initially enters the body lumen (before insertion of the plug member and carrier member), and a second greater fluid flow rate through the bleed back lumen may be detected when the plug member begins to enter the body lumen.

The plug member may be released from the carrier member within the passage, and the carrier member and/or guide member may be removed from the plug member. The plug member may include a sealing member for sealing the lumen upon removal of the guide member. Preferably, the plug member is formed at least partially from bioabsorbable material, and is left within the passage until it is absorbed by the tissue.

In accordance with yet another aspect of the present invention, an apparatus is provided for sealing a passage through tissue communicating with a body lumen. The apparatus includes a plug member including a distal end and a proximal end. The plug member may include a tapered portion terminating in the distal end, and a helical thread pattern on an outer surface of the plug member. The plug member may also include a lumen extending from the proximal end to a location proximal to the distal end.

The plug member may be continuously tapered from the proximal end to the distal end, preferably having a frustoconical shape, defining substantially blunt distal end. The lumen may communicate with a distal port that may be disposed on the distal end or offset proximally from the distal end by a predetermined distance.

The apparatus may also include a carrier member or handle device including proximal and distal ends, the plug member being coupled to the distal end of the carrier member. The carrier member may include a lumen extending between the proximal and distal ends that communicates with the lumen in the plug member. The plug member may be formed from bioabsorbable material, and/or may be releasable from the distal end of the carrier member, similar to the embodiment described above.

Other objects and features of the present invention will become apparent from consideration of the following description taken in conjunction with the accompanying drawings.

DETAILED DESCRIPTION OF THE PREFERRED EMBODIMENTS

Figure 1A:
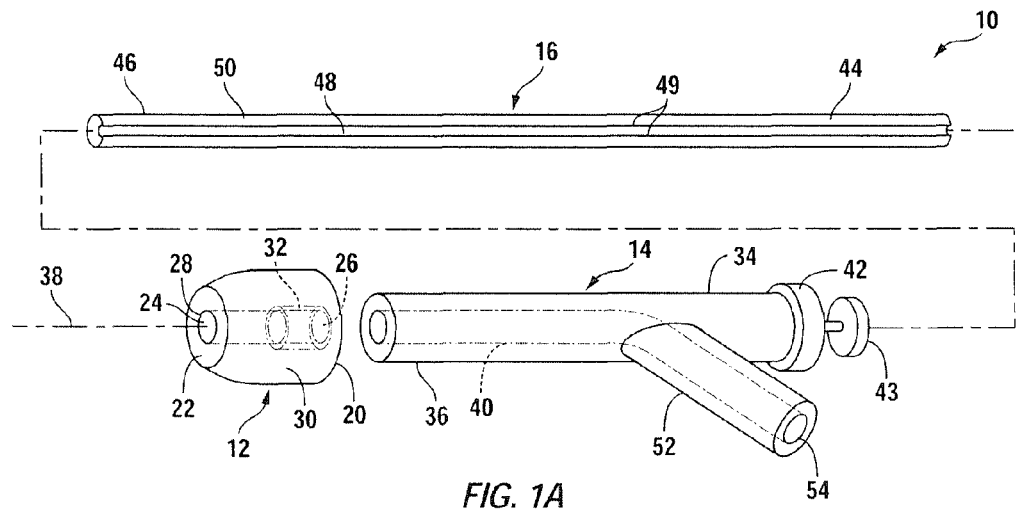
FIG. 1A is an exploded perspective view of a first preferred embodiment of an apparatus for sealing a passage through tissue, in accordance with the present invention.
Figure 1B:
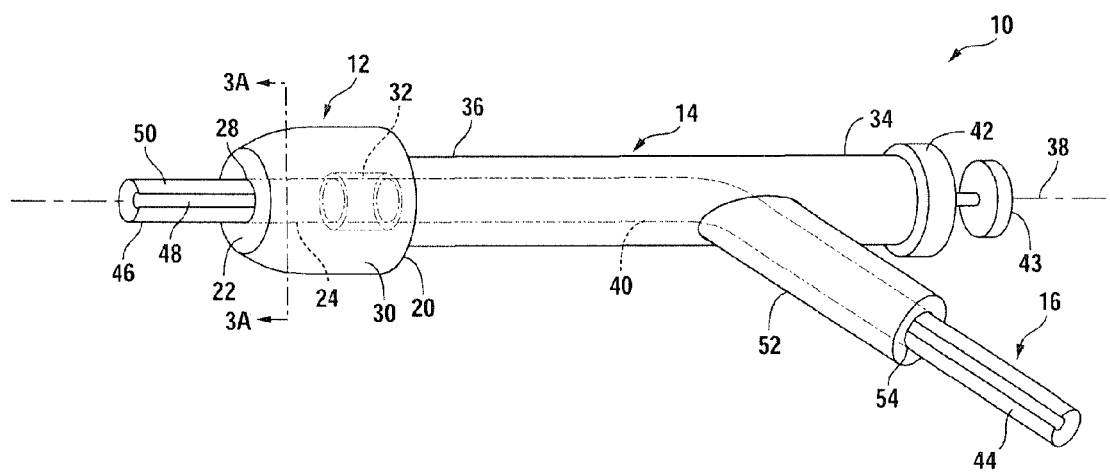
FIG. 1B is a perspective view of the assembled apparatus of FIG. 1A.

Turning now to the drawings, FIGS. 1A and 1B show a first preferred embodiment of an apparatus 10 for sealing a passage through tissue, in accordance with the present invention. Generally, the apparatus 10 includes a plug member 12, an elongate shaft or carrier member 14, and an elongate guide member 16.

The plug member 12 is a substantially rigid body, preferably having a generally cylindrical shape, including a proximal end 20, a distal end 22, and an outer surface 30. The plug member 12 includes a lumen 24 that extends between a proximal opening 26 and a distal opening or port 28.

The plug member 12 may be formed from a biocompatible material, e.g., a plastic, such as polyethylene or polyester. Preferably, the plug member 12 is formed at least partially (and more preferably entirely) from bioabsorbable material, such as collagen, polyglycolic acids (PGA's), polyactides (PLA's), and the like, that may be at least partially absorbed by the patient's body, over time. Alternatively, the plug member 12 may be a semi-rigid or flexible body or may have a substantially flexible distal tip (not shown), e.g., to facilitate atraumatic insertion of the plug member 12 into the passage. In addition or alternatively, the plug member 12 may be tapered along its length, and/or the distal end 22 may be rounded to facilitate advancement of the plug member 12 into a passage through tissue.

Preferably, the plug member 12 has a length of not more than about ten millimeters (10 mm), and more preferably between about one and ten millimeters (1-10 mm). The plug member 12 also preferably has a diameter of between about one and twenty millimeters (1-20 mm). In addition, the length and diameter may have a ratio that is not more than about two-to-one.

Figure 2A:
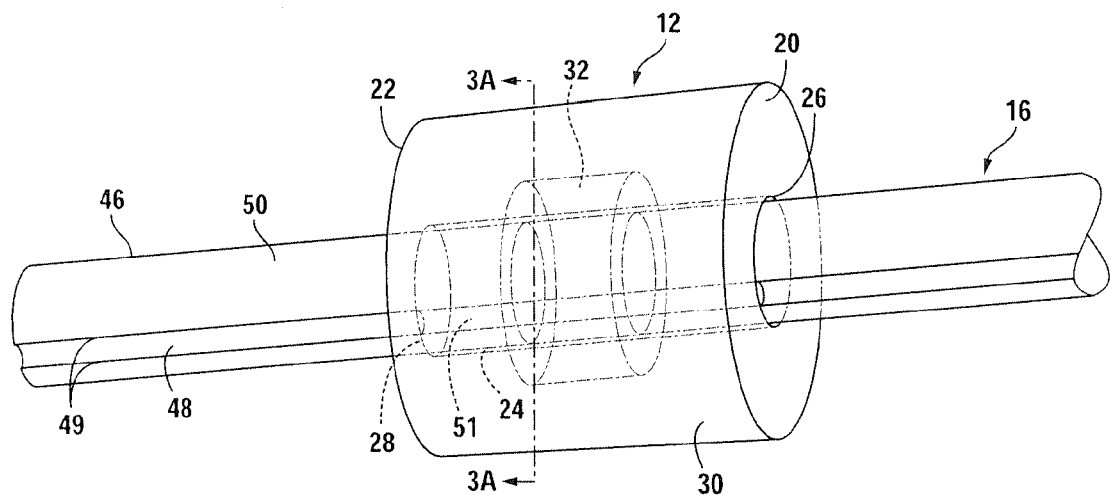
FIG. 2A is a detail of a plug member on a distal end of the apparatus of FIGS. 1A and 1B.

In one embodiment, shown in FIG. 2A, the outer surface 30 is substantially smooth, thereby facilitating direct advancement of the plug member 12 into a passage through tissue (not shown). In an alternative embodiment, shown in FIG. 2B, the plug member 12' may include a helical thread pattern 18', including one or more helical threads, that extend at least partially between its proximal and distal ends 20', 22'. The thread pattern 18' may extend completely to the distal end 22' of the plug member 12', and may be tapered at the distal end 22' to facilitate introduction into a passage through tissue (not shown). Additional information on plug members including an external helical thread pattern may be found in application Ser. Nos. 09/866,548, and 09/738,431, incorporated by reference above.

Returning to FIG. 2A (in which the carrier member 14 has been eliminated for convenience), a sealing member 32 may be provided within the lumen 24 for substantially sealing the lumen 24 from fluid flow therethrough. In a preferred embodiment, the sealing member 32 has an annular shape, and is mounted within an annular recess 33 in the lumen 24. The sealing member 32 is preferably formed from a material that expands when exposed to fluids, e.g., an expandable foam. More preferably, the sealing member 32 is also bioabsorbable, similar to the plug member 12 itself. Exemplary materials that may be appropriate for use in the sealing member 32 and/or for the plug member 12 are disclosed in U.S. Pat. No. 6,224,630, the disclosure of which is expressly incorporated herein by reference. Alternatively, the sealing member 32 may be a valve (not shown) that is biased to substantially seal the lumen 24 from fluid flow, but may be opened to facilitate introduction of one or more devices, e.g., the obturator 16 therethrough, as described further below.

In addition or alternatively, the plug member 12 may include a cavity (not shown) in the distal end 22. A material (also not shown) may be provided in the cavity, such as extra-cellular matrix material, e.g., intestinal, stomach, or bladder submucosa, collagen, an infection-resistant material, and the like, that may promote hemostasis and/or healing of the tissue. Alternatively, such material may be otherwise detachably secured to the distal end 22 of the plug member 12, either within a cavity or across the distal end 22 without a cavity. For example, the material may be secured using a biodegradable adhesive or a mechanical fastener, such as one or more clips (not shown).

Returning to FIGS. 1A and 1B, the carrier member 14 has a proximal end 34 and a distal end 36, and defines a longitudinal axis 38 that extends between the proximal and distal ends 34, 36. A lumen 40 also extends between the proximal and distal ends 34, 36 for accommodating insertion of the guide member 16 therethrough, as described further below. A handle 42 may be provided on the proximal end 34 of the carrier member 14 for facilitating manipulation of the apparatus 10.

Preferably, the carrier member 14 is a substantially rigid tubular member, formed from a biocompatible material, e.g., plastic, such as polyethylene or polyester, or metal, such as stainless steel. The carrier member 14 preferably has a cross-section that is substantially smaller than a cross-section of the plug member 12, e.g., to minimize dilation of a passage into which the apparatus 10 is inserted. In the preferred embodiment shown, the carrier member 14 may include a lateral proximal portion 52 through which the lumen 40 extends and communicates with a proximal port 54. The proximal port 54 may be connected to a valve or other device (not shown) for facilitating visual observation of fluid exiting the proximal port 54, as will be appreciated by those skilled in the art.

At least one of the plug member 12 and the distal end 36 of the carrier member 14 includes a connector. Preferably, the plug member 12 and the distal end 36 of the carrier member 14 include cooperating connectors (not shown) for releasably securing the plug member 12 to the carrier member 14, as described in application Ser. No. 09/738,431, incorporated above. Preferably, the cooperating connectors substantially couple the plug member 12 to the carrier member 14 such that the plug member 12 cannot move independently of the carrier member 14, e.g., such that the plug member 12 may be rotated only by rotating the carrier member 14.

Preferably, the handle 42 includes an actuator 43 that may be activated to release the connector(s) securing the plug member 12 to the distal end 36 of the carrier member 14. For example, the actuator 43 may include a button coupled to a control rod or wire (not shown) that extends through the carrier member 14 to the distal end 36. Upon depression of the button, the control rod may be moved, thereby disengaging the connector on the carrier member 14 from the plug member 12 or a mating connector (not shown) on the plug member 12. In another alternative, the distal end 36 of the carrier member 14 and the plug member 12 may include mating threads (not shown) such that the carrier member 14 may be rotated with respect to the plug member 12 to release the plug member 12. In this embodiment, the mating threads should wind helically in the same direction as the thread pattern 18 on the plug member 12 to ensure that the plug member 12 is not released prematurely from the carrier member 14.

The guide member 16 is an elongate member, e.g., formed from flexible or semi-rigid material, having a proximal end 44 and a substantially atraumatic and/or flexible distal tip 46, e.g., having a size for insertion into a passage through tissue into a blood vessel or other body lumen (not shown). An elongate groove 48 defined by opposing edges 49 is provided in an external surface 50 that extends from the proximal end 44 to the distal tip 46. Alternatively, the groove 48 may terminate before to the distal tip 46, e.g., a predetermined distance proximal to the distal tip 46 (not shown).

The guide member 16 has a size and shape for slidable insertion through the lumen 40 of the carrier member 14 and through the lumen 24 of the plug member 12. During use, the guide member 16 may be inserted through the carrier member 14 such that the distal tip 46 of the guide member 16 extends beyond the distal end 22 of the plug member 12, as shown in FIG. 1B.

Figure 3A:
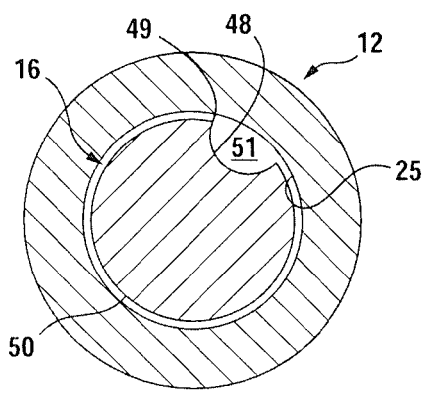
FIG. 3A is a cross-sectional view of the apparatus of FIG. 1B taken along line 3A-3A.
Figure 3B:
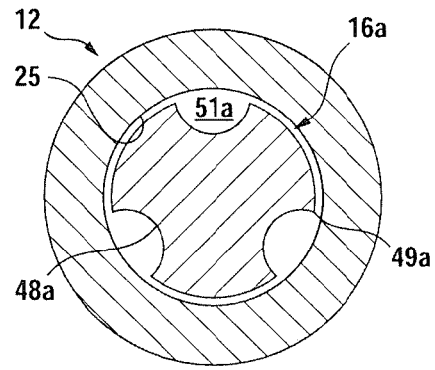
FIGS. 3B-3F are cross-sectional views of the apparatus of FIG. 1B, showing alternate embodiments of a guide member.
Figure 3C:
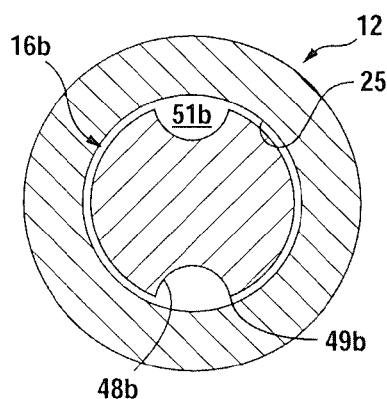
Figure 3D:
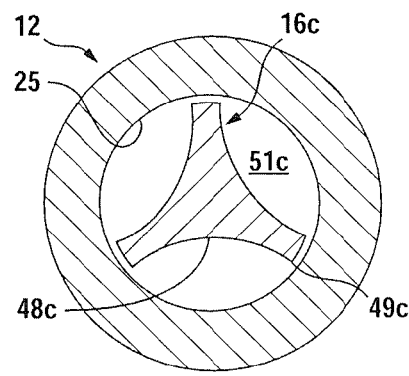
Figure 3E:
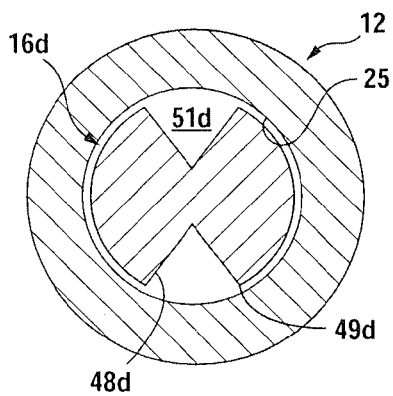
Figure 3F:
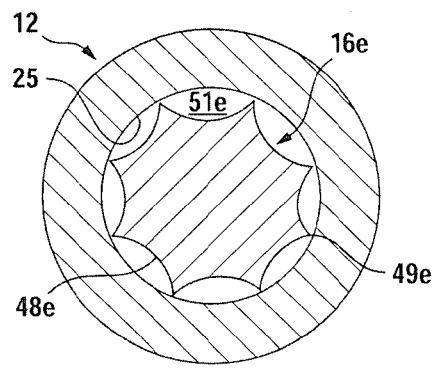

Preferably, as shown in FIG. 3A, the lumen 24 in the plug member 12 has a cross-section, e.g., diameter, similar to that of the guide member 16 such that edges 49 of the groove 48 slidably engage an inner wall 25 of the plug member 12. Thus, the plug member 12 and guide member 16 may together define a lumen 51, which is generally referred to as a bleed back lumen (although it may receive other fluids in addition to or instead of blood). Similarly, the lumen 40 in the carrier member 14 may also have a cross-section similar to and aligned with the lumen 24 in the plug member 12, thereby further defining the bleed back lumen 51.

In alternative embodiments, shown in FIGS. 3B-3F, the guide member $16_a$-$16_e$ may have one of a variety of cross-sections, thereby providing one or more bleed back lumens $51_a$-$51_e$ defined by edges $49_a$-$49_e$ of one or more respective grooves $48_a$-$48_e$ in the guide member $16_a$-$16_e$ and an inner wall 25 of the plug member 12. In addition, the grooves 48 may have one of a variety of shapes, such as the exemplary concave, notched, or flat cross-sections shown in FIGS. 3B-3F. Thus, any number of bleed back lumens, having any desired shape may be provided in the apparatus 10.

Turning to FIGS. 4A-4D, during use, the apparatus 10 may be used to seal and/or close a passage through tissue 96, such as a puncture 92 communicating with a blood vessel 90 or other body lumen. The puncture 92 may be used to provide percutaneous access through a wall 98 of the vessel 90 into the vessel lumen 94. For example, the puncture 92 may facilitate performing an endovascular procedure within a patient's vasculature, such as angioplasty, stenting, atherectomy, and the like, or may otherwise provide access via the vessel 90 to a region within the patient's body.

Upon completion of the procedure, any instruments, such as an introducer sheath (not shown), may be removed from the vessel 90 and puncture 92. If a guidewire 102 is used during the procedure, the guidewire 102 may be removed before delivering the plug member 12. Alternatively, however, the guidewire 102 may be used to guide the plug member 12 into position, as described below. In a further alternative, an introducer sheath (not shown), such as that used to previously introduce instruments into the vessel 90 may be left in place, and the guidewire 102 may be removed.

Figure 4A:
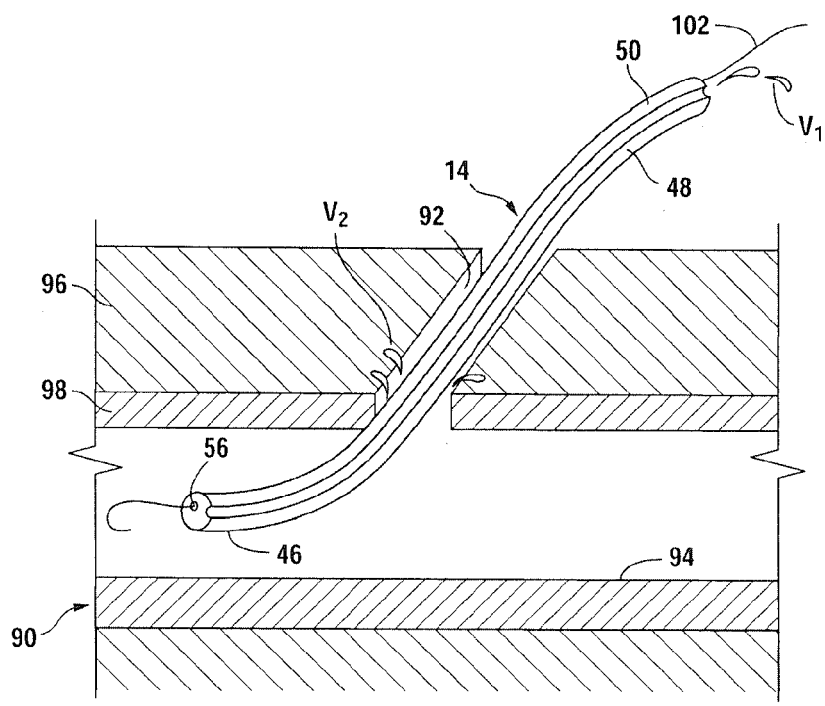
FIGS. 4A-4D are cross-sectional views showing a plug member on the apparatus of FIGS. 1A and 1B being used to seal an opening in a wall of a blood vessel.

Initially, the guide member 16 is introduced into the puncture 92, for example, by inserting the distal tip 46 of the guide member 16 into the puncture 92 and advancing the distal tip 46 until it enters the vessel 90, as shown in FIG. 4A. If the guidewire 102 is in place, generally as shown, the guidewire 102 may be backloaded into a guidewire lumen 56 in the guide member 16 in a conventional manner before inserting the distal tip 46 into the puncture 92. Alternatively, if an introducer sheath is left in place, the guide member 16 may be advanced through a lumen of the introducer sheath.

As the distal tip 36 enters the vessel 90 (e.g., over the guidewire 102 or through an introducer sheath), capillary action may cause a relatively small amount of blood, represented by to travel proximally along the groove 48 to the proximal end 44 of the guide member 16. Because the groove 48 does not provide a substantially enclosed lumen, however, much (and preferably most) of the blood entering the puncture 92 may be dispersed within subcutaneous tissue, e.g., adjacent to the wall 98 of the vessel 90, as represented by $v_2$, and not travel to the proximal end 44 of the guide member 16. If a guidewire and/or an introducer sheath is used to direct the guide member 16 into the vessel 90, they may be removed once the distal tip 36 is positioned within the vessel 90.

Figure 4B:
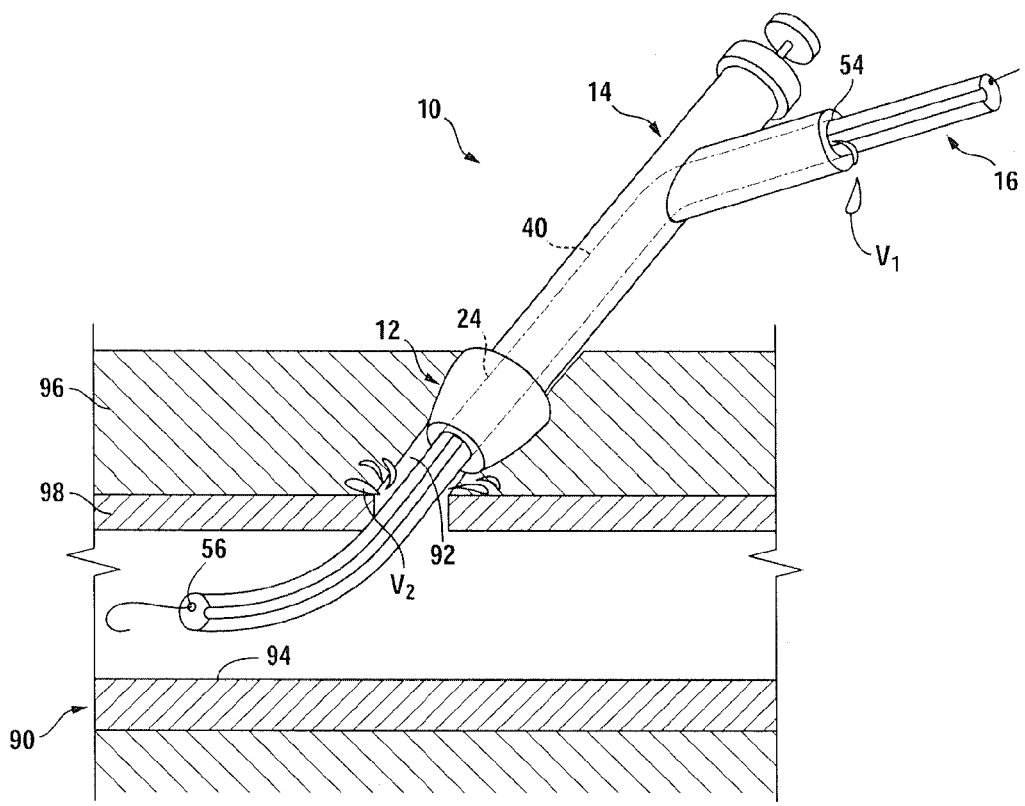

The plug member 12 may then be advanced over the guide member 16 into the puncture 92, as shown in FIG. 4B. Preferably, the proximal end 46 of the guide member 16 is inserted into the lumen 24 in the plug member 12. The plug member 12 is then advanced over the guide member 16 and into the puncture 92 until the proximal end 46 of the guide member 16 passes through the lumen 40 in the carrier member 14 and exits the lumen 40 at the proximal end 36 of the carrier member 14. Optionally, the carrier member 14 may not include a lumen and a separate lumen member (not shown) may be provided that communicates with the lumen 24 in the plug member 12.

Preferably, the lumens 24, 40 in the plug member 12 and/or the carrier member 14 have a cross-section, e.g., diameter, similar to that of the guide member 16 such that the groove 48 and the lumens 24, 40 define a bleed back lumen 51, as described above. Thus, as the plug member 12 is advanced over the guide member 16, the bleed back lumen 51 is also advanced distally.

Figure 2B:
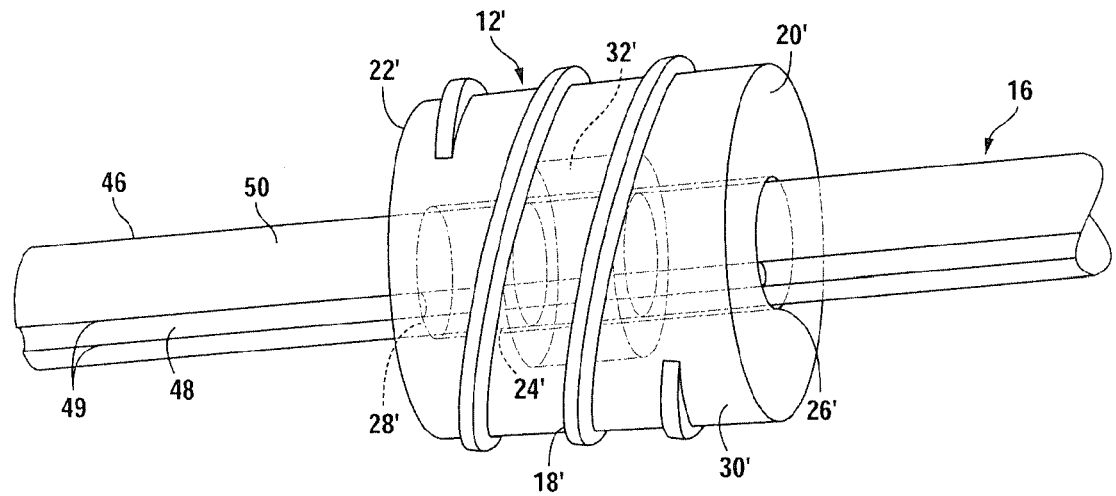
FIG. 2B is a detail of an alternative embodiment of a plug member on a distal end of the apparatus of FIGS. 1A and 1B.

If the plug member 12 includes a thread pattern 18 (as shown in FIG. 2B), the carrier member 14 may be rotated in a first direction to thread the plug member 12 into the puncture 92. Because the plug member 12 is coupled to the carrier member 14, as the carrier member 14 is rotated, the plug member 12 is rotated and threaded into the puncture 92 towards the vessel 90. Consequently, the outer surface 30 and thread pattern 18 of the plug member 12 may engage tissue 96 surrounding the puncture 92, thereby substantially sealing the puncture 92 from fluids, such as blood, within the vessel 90.

One advantage of providing an external thread on the plug member 12 is that the thread pattern 18 may facilitate advancement of the plug member 12 through layers of tissue (not shown) towards the vessel 90. For example, the tissue 96 may include one or more intermediate layers of fascia or other tissue structures disposed between layers of fat (also not shown). The fascia layer may be relatively thin, yet resilient and tough, and therefore it may be difficult to advance a device axially through the layer without deflecting the layer towards the vessel 90.

Figure 4C:
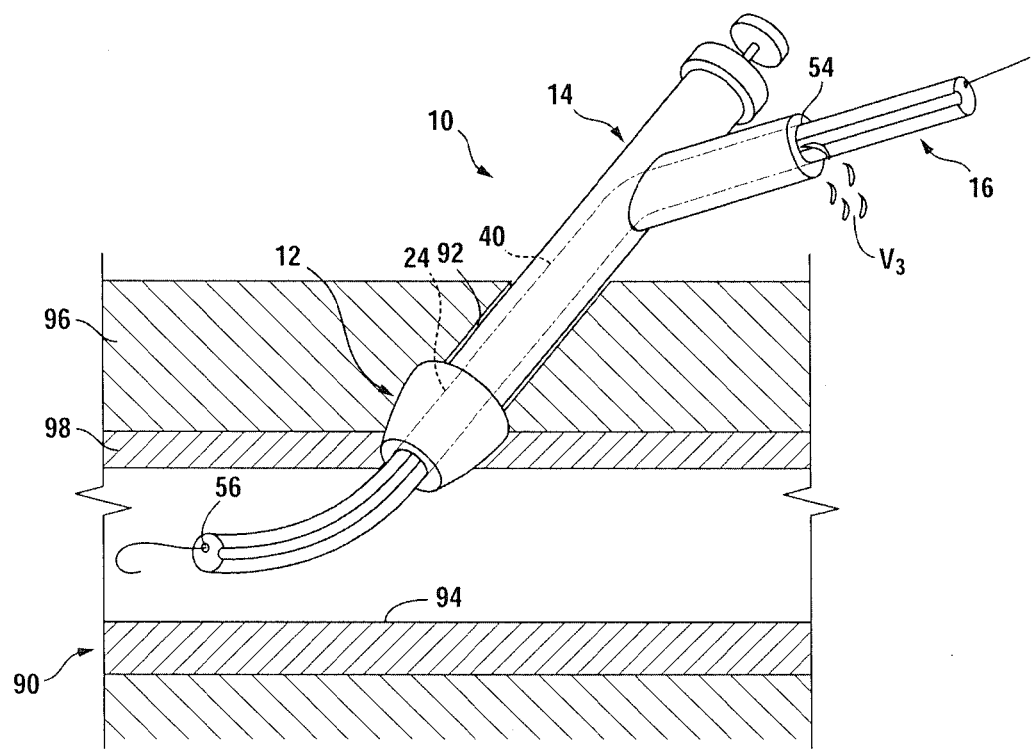

When the plug member 12 is advanced through the wall 98 of the vessel 90, as shown in FIG. 4C, the bleed back lumen 51 may become exposed to fluid, e.g., blood, within the vessel 90. Because of internal blood pressure, the fluid may enter the bleed back lumen 51 (not shown, see FIG. 2A), pass through the lumens 24, 40 in the plug member 12 and the carrier member 14, and exit the proximal port 54 of the carrier member 14, as represented by $v_3$, thereby providing a visual indication that the vessel 90 has been attained. If a relatively low rate of fluid flow was previously observed, a substantially higher rate of fluid flow may be observed, because fluid entering the puncture 92 may no longer be dispersed within the subcutaneous tissue, but pass instead through the bleed back lumen 51. This visual indication from the proximal port 54 may provide feedback that the distal end 22 of the plug member 12 has reached the vessel 90, as will be appreciated by those skilled in the art.

If desired, the carrier member 14 may then be withdrawn partially to move the plug member 12 to a predetermined deployment depth, e.g., offset proximally form the wall 98 of the vessel 90. For example, bleed back may occur when the plug member 12 is within or in close proximity to the vessel 90, as shown in FIG. 4B. If the plug member 12 includes an external thread, rotation of the apparatus 10 may be reversed, i.e., in a second direction opposite the first direction, to withdraw the plug member 12 a predetermined distance relative to the vessel 90. If no external thread is provided, the carrier member 14 may simply be pulled proximally. Otherwise, the plug member 12 may be left in place, e.g., in contact with the wall 98 of the vessel 90.

Once the desired deployment location is attained, the plug member 12 may be released from the carrier member 14, e.g., by depressing actuator 43. The guide member 16 may be withdrawn from the plug member 12 and carrier member 14 either before or after releasing the plug member 12. The sealing member 32 preferably substantially seals the lumen 24 within the plug member 12 thereafter to prevent fluid within the vessel 90 from passing therethrough to leak from the puncture 92.

For example, as explained above, the sealing member 32 may include a material that expands when exposed to fluid. As the guide member 16 is withdrawn, fluid, e.g., blood, may flow proximally through the lumen 24 in the plug member 12, e.g., until it encounters the sealing member 32. Although a relatively small amount of fluid may pass beyond the sealing member 32, the sealing member 32 may expand relatively quickly due to the fluid contact until it substantially seals the lumen 24. Alternatively, the sealing member 32 may be a valve that may automatically open to accommodate the guide member 16, but may automatically close upon withdrawal of the guide member 16. In a further alternative, the sealing member 32 may be manually actuated by the user.

Figure 4D:
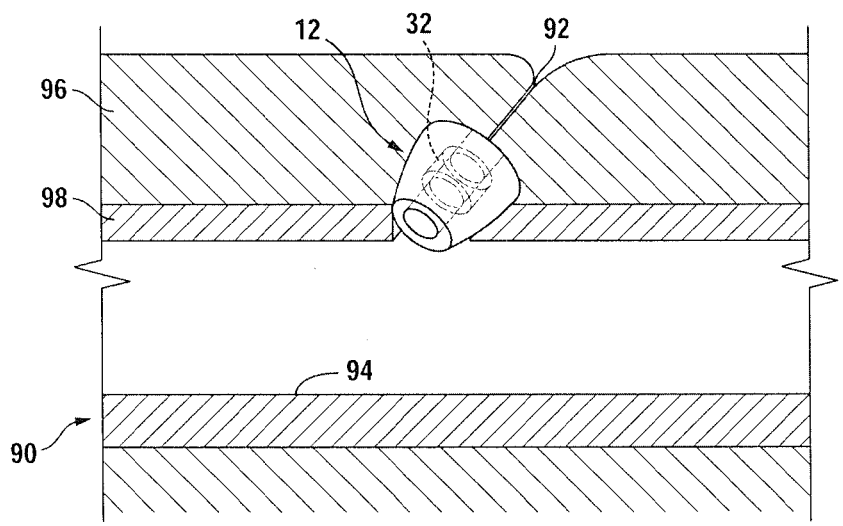

Finally, as shown in FIG. 4D, the carrier member 14 and the guidewire 102 (if still in place) may be withdrawn, leaving the plug member 12 in place to substantially seal the puncture 92. If the plug member 12 is bioabsorbable, it may remain within the puncture 92 as the tissue heals, thereby allowing the wall 98 of the vessel 90 and tissue 96 surrounding the passage 92 to at least partially heal before the plug member 12 is absorbed. Alternatively, the plug member 12 may be retrieved once the tissue between the plug member 12 and the vessel 90 has substantially healed, as described in the applications incorporated above.

Turning to FIGS. 5A-5D, yet another embodiment of an apparatus 110 is shown that includes a plug member 112 and a handle device 114. The plug member 112 includes a body, preferably formed from bioabsorbable material, including a proximal end 120 and a distal end 122. An outer surface 130 of the plug member 112 may be substantially smooth or may include a helical thread pattern (riot shown) extending along the outer surface 130 at least partially between the proximal and distal ends 120, 122, similar to the embodiment described above.

In addition, the plug member 112 includes a lumen 124 that extends between a proximal opening 126 and a distal opening 128 generally parallel to a longitudinal axis 138. An inner lip 125 is provided within the lumen 124, e.g., adjacent the distal end 122 of the plug member 112, which may be a continuous annular ridge or a plurality of tabs.

Figure 7A:
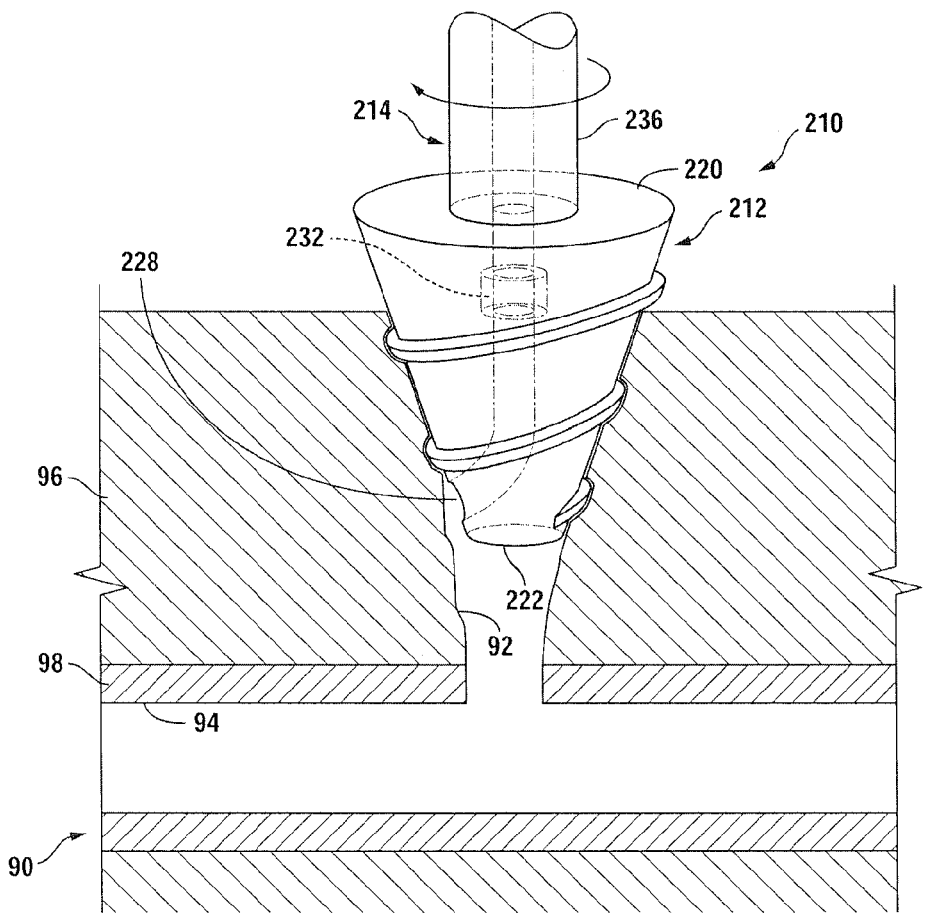
FIGS. 7A and 7B are cross-sectional views showing a plug member on the apparatus of FIG. 6 being used to seal an opening in a wall of a blood vessel.
Figure 7B:
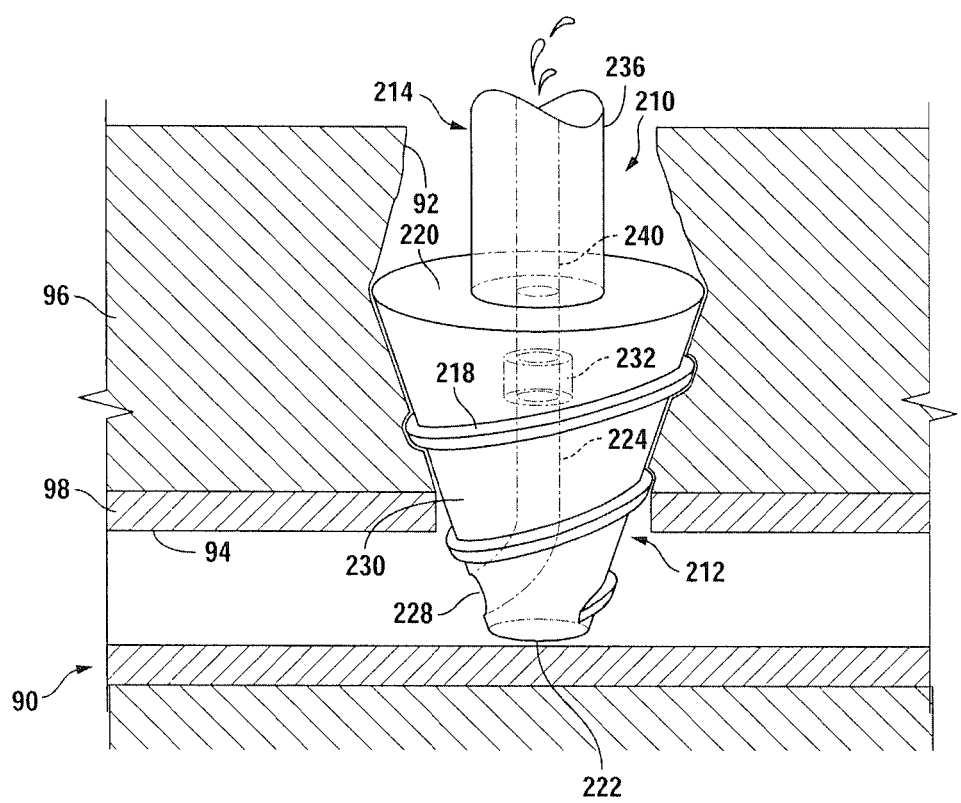

A sealing member 132 is disposed within the lumen 124 in an open position (shown in FIG. 7A) adjacent the inner lip 125. The sealing member 132 is a generally annular-shaped member, preferably a coil of material including one or more overlapping layers, which may be formed from a biocompatible, and preferably a bioabsorbable material, similar to the plug member 112. Alternatively, the sealing member 132 may be an enclosed ring that may be formed from semi-rigid or flexible material. In the open position, the lumen 124 is substantially open, i.e., the sealing member 132 does not generally obstruct the lumen 124. The sealing member 132 is compressible distally against the lip 125 to become compressed or wedged therein (as shown in FIG. 7B), thereby defining a closed position for substantially sealing the lumen 124 from fluid flow therethrough.

The handle device 114 includes an outer carrier tube 134, and an inner delivery tube 136, the inner tube 136 being coaxially and/or slidably disposed within the outer tube 134. The handle device 114 may include a handle and/or actuator (not shown) on a proximal end of the handle device 114 for manipulating the handle device 114 and/or for controlling movement of the inner tube 136 relative to the outer tube 134. A distal end 140 of the outer tube 134 may be received in an annular recess 127 to couple the plug member 112 to the handle device 114. The distal end 140 may frictionally engage a wall of the recess 127, e.g., providing a desired resistance to removing the distal end 140 from the recess 127. In addition or alternatively, the connector at the distal end 140 and/or the plug member 112 may include one or more detents 146, similar to the embodiment described above.

A distal end 142 of the inner tube 136 preferably has a size for being slidably received within the lumen 124 and substantially abutting the sealing member 132. The inner tube 136 preferably includes a lumen 144 that communicates with the lumen 124. Thus, the lumens 144, 124 may provide a lumen for receiving a guide member (not shown), such as that shown and described in connection with FIG. 1A.

Use of the apparatus 110 proceeds similar to the previous embodiment, except that the sealing member 132 is manually activated, rather than being activated automatically upon fluid contact. The apparatus 110 is assembled by inserting the distal end 140 of the outer tube 134 into the recess 127 and the distal end 142 of the inner tube 136 into the lumen 124, as shown in FIG. 7A. A guide member (not shown) may be directed into a passage communicating with a vessel, e.g., through an introducer sheath, which is then removed once a distal end of the guide member is positioned within the vessel, similar to the previous embodiment.

The plug member 112 is inserted into the passage over the guide member until the distal end 122 of the plug member 112 enters the vessel. As the plug member 112 enters the vessel, a bleed back lumen defined by a groove (not shown) in the guide member and the wall of the lumen 124 becomes exposed to the interior of the vessel, causing fluid to flow into the bleed back lumen to a proximal outlet port or other bleed back indicator (not shown) on the handle device 114.

Figure 5A:
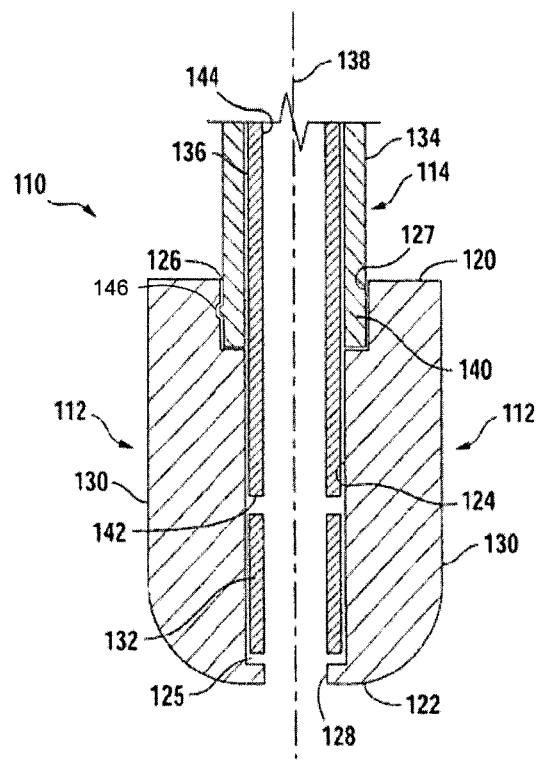
FIGS. 5A and 5B are cross-sectional views of a distal end of a second preferred embodiment of a plug member including a sealing member that is open and sealing a lumen, respectively, in accordance with the present invention.
Figure 5B:
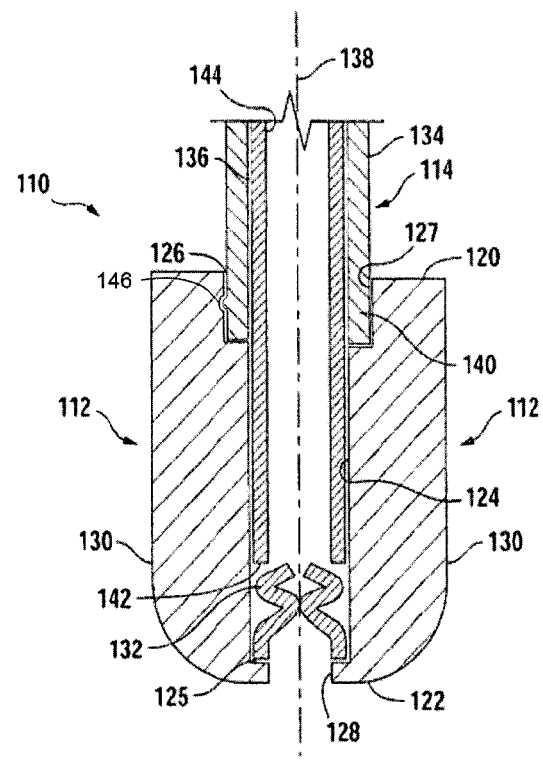

The inner tube 136 may then be advanced distally relative to the outer tube 134, thereby engaging the sealing member 132 and forcing it distally against the inner lip 125. Because of its inherent flexibility and/or because of its coil shape, the sealing member 132 may compress and/or become crushed, wedging the sealing member 132 within the lumen 124 and sealing the lumen 124 from fluid flow therethrough, as shown in FIG. 5B. In addition, a distal portion of the sealing member 132 may attached to an inner wall of the plug member 112 defining the lumen 124, e.g., by an adhesive, sonic welding, and the like. Alternatively, if the sealing member 132 is attached to the inner wall, the lip may be eliminated (not shown).

The plug member 112 may be released from the handle device 114, e.g., by withdrawing the outer tube 136 and/or by releasing connectors securing the plug member 112 to the distal end 140 of the outer tube 134. The handle device 114 may then be withdrawn form the passage, leaving the plug member 112 in place, similar to the embodiment described above.

Figure 6:
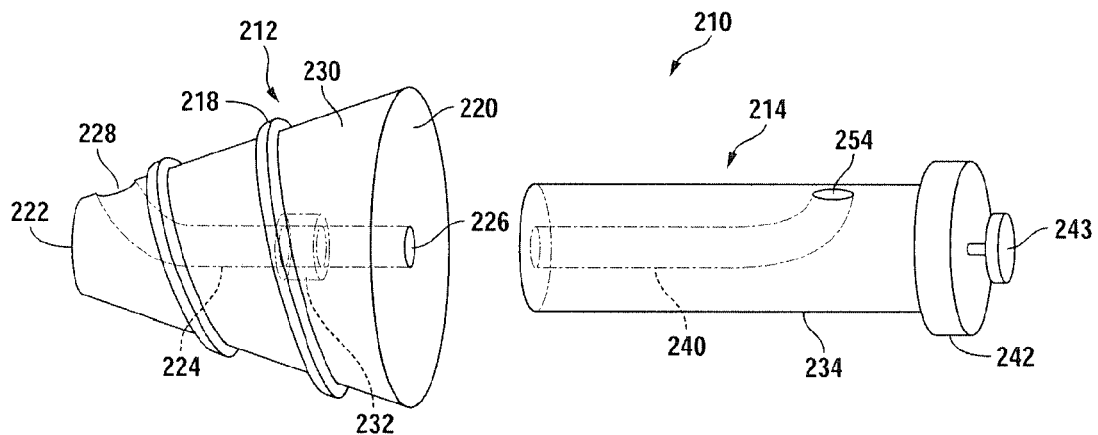
FIG. 6 is an exploded perspective view of a third preferred embodiment of an apparatus for sealing a passage through tissue, in accordance with the present invention.

Turning to FIG. 6, another embodiment of an apparatus 210 is shown that includes a plug member 212 and a handle device 214. The plug member 212 includes a tapered body, preferably formed from bioabsorbable material, including a proximal end 220 and a distal end 222. Preferably, the plug member 212 is continuously tapered from the proximal end 220 towards the distal end 222, although alternatively, only a distal portion of the plug member may be tapered (not shown). The plug member 212 may have a substantially constant taper or the taper rate may vary along the length of the plug member 212 (not shown). The distal end 222 may be substantially rounded or blunt, may include a concave distal tip as shown, and/or may be pointed (not shown).

In addition, the plug member 212 includes a lumen 224, and may include a sealing member 232 disposed within the lumen 224, similar to the embodiments described above. The lumen 224 communicates with a distal port 228 that is located on or adjacent the distal end 222 of the plug member 212.

A helical thread pattern 218 extends along an outer surface 230 of the plug member 212 at least partially between the proximal and distal ends 220, 222. Alternatively, the outer surface 230 may be substantially smooth or may include gripping elements for allowing distal advancement but preventing proximal withdrawal of the plug member 212 from within a passage through tissue, similar to the embodiments described above.

The handle device 214 is an elongate member having a proximal end 234, a distal end 236, and a lumen 240 extending therebetween. Preferably, the plug member 212 and the handle device 214 include cooperating elements (not shown) for coupling the plug member 212 to the handle device 214, i.e., to prevent rotation of the plug member 212 relative to the handle device 214. For example, cooperating connectors (not shown) may be provided for releasably securing the plug member 212 to the distal end 236 of the handle device 214, similar to the embodiment described above. If the plug member 212 has an internal sealing member (not shown), the handle device 214 may include an internal member, e.g., inner tube (also not shown), for wedging or otherwise activating the sealing member.

Turning to FIGS. 7A-7B, during use, the apparatus 210 may be used to seal and/or close a passage through tissue 96, such as a puncture 92 used to access a blood vessel 90 during an endovascular procedure, similar to the embodiment described above. Upon completion of the procedure, any instruments, such as an introducer sheath, a guidewire, and the like (not shown), may be removed from the vessel 90 and puncture 92.

As shown in FIG. 7A, the distal end 222 of the plug member 212 may be inserted into the puncture 92, and the handle device 214 rotated in a first direction to advance the plug member 212 into the puncture 92. Because the plug member 212 is coupled to the handle device 214, rotation of the handle device 214 preferably threads the plug member 212 into the puncture 92 towards the vessel 90. Consequently, the outer surface 230 and/or the thread pattern 218 of the plug member 212 may engage tissue 96 surrounding the puncture 92, thereby substantially sealing the puncture 92 from fluids, such as blood, within the vessel 90. In addition, the thread pattern 218 may facilitate advancing the plug member 212 through any intervening layers of tissue, e.g., one or more layers of fascia (not shown), similar to the embodiments described above.

As shown in FIG. 7B, when the distal end 222 of the plug member 212 is advanced through the wall 98 of the vessel 90, the distal port 228 becomes exposed to fluid, e.g., blood, within the vessel 90. Because of internal blood pressure, the fluid may enter the distal port 228 and pass through the lumens 224, 240, thereby providing a visual indication that the vessel 90 has been attained, similar to the embodiment described above.

The plug member 212 may then be released from the handle device 214, e.g., by activating an actuator (not shown, see FIG. 6) on the proximal end of the handle device 114, and the handle device 214 withdrawn from the passage 92. Preferably, the distal end 222 of the plug member 212 does not extend substantially into the vessel 90, thereby minimizing obstruction of the lumen 94. The tapered profile of the plug member 212 may substantially anchor the plug member 212 within the passage 92 and/or enhance sealing the passage 92 from fluid flow.

Alternatively, after bleed back indicates that the distal end 22 is located within the vessel 90, rotation of the handle device 214 may be reversed, i.e., in a second direction opposite the first direction, to withdraw the plug member 212 a predetermined distance relative to the vessel 90. Once the desired deployment location is attained, the plug member 212 may be released from the handle device 214. The handle device 214 may be withdrawn, leaving the plug member 212 in place to substantially seal the passage 92.

As fluid flows through the lumen 224, the sealing member 232 may expand to substantially seal the lumen 224 to prevent further fluid within the vessel 90 from passing therethrough to leak from the puncture 92. Alternatively, the lumen 224 may be sufficiently small that the sealing member 232 may be eliminated, and may seal as hemostasis occurs.

In a further alternative, the sealing member 132 may be manually wedged or otherwise closed to seal the lumen 124.

If the plug member 212 is bioabsorbable, it may remain within the puncture 92 as the tissue heals, thereby allowing the wall 98 of the vessel 90 and tissue 96 surrounding the passage 92 to at least partially heal before the plug member 112 is absorbed. Alternatively, the plug member 212 may be retrieved once the tissue between the plug member 212 and the vessel 90 has substantially healed.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An apparatus for sealing a passage through tissue, comprising:
    an elongate member having a proximal end, a distal end, and a lumen extending between the proximal and distal ends; and
    a plug member releasably secured to the distal end of the elongate member by a connector configured to prevent the plug member from moving independently of the elongate member, the plug member comprising a distal port therein in communication and coaxially aligned with the lumen, the distal port configured to be open when the plug member is being delivered and the plug member having a cross-section larger than a cross-section of the elongate member when the plug member is releasably secured to the distal end of the elongate member prior to being inserted within the passage and after being released, wherein the plug member tapers along a longitudinal axis from a proximal end of the plug member to the distal end of the plug member such that a radial dimension perpendicular to the longitudinal axis at any location is not greater than a corresponding radial dimension of a proximal location and the distal end of the plug member is smaller than the proximal end of the plug member, the longitudinal axis being established by the lumen of the elongate member.

2. The apparatus of claim 1, wherein the plug member comprises a passage therein extending between the distal port and the lumen.

3. The apparatus of claim 2, further comprising a sealing member disposed in the plug member passage for substantially sealing the passage from fluid flow therethrough.

4. The apparatus of claim 3, wherein the sealing member comprises a material that is expandable when exposed to fluid for substantially sealing the plug member passage.

5. The apparatus of claim 3, wherein the sealing member is biased towards a first configuration for substantially sealing the plug member passage from fluid flow therethrough, and is movable to a second configuration for accommodating introduction of one or more devices through the plug member passage.

6. The apparatus of claim 3, wherein the sealing member comprises a valve.

7. The apparatus of claim 3, wherein the plug member passage includes a tapered portion reducing in cross-section, and wherein the sealing member comprises a generally annular-shaped member disposed adjacent a wide end of the tapered portion of the plug member passage, the annular-shaped member being movable into the tapered portion for substantially sealing the plug member passage.

8. The apparatus of claim 7, further comprising an activation element coupled to the elongate member, the activation element extending into the plug member passage for moving the sealing member into the tapered portion for substantially sealing the plug member passage.

9. The apparatus of claim 2, further comprising an inner elongate member insertable through the lumen of the elongate member such that a distal end of the inner elongate member is disposed beyond the distal end of the plug member.

10. The apparatus of claim 9, wherein the distal end of the inner elongate member comprises a location indicator for identifying when the distal end of the plug member is disposed adjacent a body lumen.

11. The apparatus of claim 10, wherein the inner elongate member comprises a tubular member including a bleed back lumen, and wherein the location indicator comprises a bleed back port on the distal end of the tubular member, the bleed back port being in communication with the bleed back lumen.

12. The apparatus of claim 10, wherein the location identifier comprises an expandable member, the expandable member being expandable when the distal end is disposed within a body lumen for providing tactile feedback of a location of the distal end of the plug member with respect to the body lumen.

13. The apparatus of claim 9, wherein the inner elongate member comprises an obturator including a substantially atraumatic distal tip.

14. The apparatus of claim 9, further comprising a valve in the plug member passage for substantially sealing the passage yet accommodating insertion of the inner elongate member therethrough.

15. The apparatus of claim 1, wherein the elongate member comprises an actuator for releasing the plug member from the distal end of the elongate member.

16. The apparatus of claim 1, further comprising a cooperating connector on the distal end of the elongate member for releasably securing the plug member to the distal end of the elongate member.

17. The apparatus of claim 1, wherein the plug member comprises an interior cavity, and wherein the elongate member comprises an engagement element extending from the distal end thereof for insertion into the cavity, the engagement element being expandable and collapsible for engaging and disengaging an interior wall of the plug member, thereby selectively securing the plug member to and releasing the plug member from the distal end of the elongate member, respectively.

18. The apparatus of claim 1, wherein the plug member comprises bioabsorbable material.

* * * * *